United States Patent [19]

Scherr

[11] Patent Number: 4,761,281

[45] Date of Patent: Aug. 2, 1988

[54] VACCINE FROM DIROFILARIA EXTRACTS

[75] Inventor: George H. Scherr, Park Forest, Ill.

[73] Assignee: ImmunoMed Corporation, Tampa, Fla.

[21] Appl. No.: 854,853

[22] Filed: Apr. 22, 1986

[51] Int. Cl.$^4$ .................... A61K 39/00; A61K 39/002
[52] U.S. Cl. ........................................ 424/88; 424/85; 530/395
[58] Field of Search ..................... 424/85, 88; 530/395

[56] References Cited

U.S. PATENT DOCUMENTS

| | | | |
|---|---|---|---|
| 3,075,883 | 1/1963 | Scherr | 424/88 |
| 3,839,555 | 10/1974 | Billiau et al. | 424/88 X |
| 3,925,544 | 12/1975 | Schechmeister et al. | 424/89 |
| 4,568,639 | 2/1986 | Lew | 424/88 X |
| 4,656,251 | 4/1987 | Mosier | 424/88 X |

FOREIGN PATENT DOCUMENTS 8436095 12/1985 Australia .
0142345 5/1985 European Pat. Off. .

OTHER PUBLICATIONS

Japan J. Exp. Med., 35, No. 2, 125–132, (1965), Sawada et al.
Journal of Immunology, 133, No. 2, 975–980, Aug., 1984, Boto et al.
Acta Tropica, 42, 63–70, (1985), Grieve et al.
Acta Veterinaria, 33, 5–6 No., pp. 315–322, (1983), Jovanovic.

*Primary Examiner*—Howard E. Schain
*Attorney, Agent, or Firm*—Pettis & McDonald

[57] ABSTRACT

A vaccine for protecting animals against infection by Dirofilaria which comprises fractions of extracts of the adult organisms of Dirofilaria.

24 Claims, No Drawings

VACCINE FROM DIROFILARIA EXTRACTS

FIELD OF THE INVENTION

This invention relates to a preparation of an antigenic component for use in a vaccine for the prevention of parasitic disease caused by Dirofilaria. More particularly, it relates to the preparation of antigens which can be used to vaccinate as a preventative against subsequent infection by the disease entity but also may be utilized as a vaccine to inhibit the course of development of the parasite in the early pre-patent stages of the disease cycle of the organism.

BACKGROUND OF THE INVENTION

Dog heartworm (*Dirofilaria immitis*) is a parasite which principally affects dogs but also has been shown to infect other animals such as cats, foxes, raccoons, ferrets, and even man. Other species of Dirofilaria infect additional hosts. For example, *Dirofilaria filaria* causes parasitic disease in sheep; *D. viviparus* causes parasitic disease in cows.

The life cycle of Dirofilaria is instituted through the bite of a mosquito which had previously bitten an infected animal. The infective larvae remain in the mosquito where they undergo three molts, after which the infective larvae migrate to the mosquitos' proboscis. The larvae are then ready to be transmitted to another host. The entire maturation process in the mosquito takes anywhere from 7–14 days.

The infective larvae enter an animal following the bite of a mosquito and then pass through three additional molts after which the adolescent parasites migrate to the heart where they will undergo final maturation. Approximately 25–37 weeks will normally transpire following infection, either as a result of infected mosquitoes biting a host or due to subcutaneous injection of appropriate larvae into animals, before microfilaria can be detected by microscopy in the blood of animals so infected.

There have been numerous attempts to prepare antigenic material as immunizing agents against Dirofilaria (Otto, in G. J. Jackson et al., Eds, Immunity to Parasitic Animals, Appleton-Century-Crofts, N.Y., pp. 963–980, 1970) reviewed attempts up to that time to immunize dogs against *D. immitis* and reported that the use of material from adult parasites had been unsuccessful.

Hyong-Sun et al. (in Canine Heartworm Disease, The Current Knowledge, Bradley and Pacheco, Eds, U. of Florida, Gainesville, 1972, pp. 55–67) utilized viable microfilaria as a possible vaccine for dog heartworm. They immunized dogs using seven vaccinations of microfilaria at three-day intervals into animals which were subsequently challenged with infectious larvae from laboratory-raised mosquitoes. The vaccinated animals showed microfilaria following challenge about two weeks after the unvaccinated controls and showed fewer microfilaria. However, this vaccination program showed that the viable microfilaria as a vaccine had little if any effect in altering the numbers of adult worms found in the vaccinated groups and the control groups which were not vaccinated.

Hyong-Sun et al. also attempted immunization of dogs with 15 kilorads (Kr) irradiated microfilaria but found that this level of irradiation was not lethal to all of the infectious larvae and, therefore, in the control groups so vaccinated but unchallenged, some of the dogs were ultimately found to have adult worms. The vaccine, therefore, was not effective.

Jovanovic, *Acta Veterinaria* 33(5–6):315–322 (1983), report attempts to vaccinate sheep against infection by *D. filaria*.

Sawada et al., *Japan J. Expt. Med.* 35(2): 125–132 (1965) (Chem. Abstr. 63: 16947), report isolation and purification of an antigen for an intradermal skin test. The antigen is extracted from a *D. immitis* homogenate with phosphate buffer (pH 7.2) and purified by a series of filtration and chromatographic procedures.

Boto et al., *J. Immunol.* 133(2): 975–980(1984), report analyses of *D. immitis* antigens prepared by detergent extraction (pH 7.4) of a *D. immitis* homogenate.

Maggio, European Patent Application No. (EP-A) 142,345, report published May 22, 1985, disclose use of anti-idiotypic monoclonal antibodies. Included in the disclosure are antibodies raised against a fraction of a *D. immitis* homogenate which is soluble at pH 3.5.

In Australian Patent Application No. 84-36-095 is disclosed a diagnostic assay employing an antibody raised against a *D. immitis* extract. The extract is prepared by extraction of an adult *D. immitis* homogenate with phosphate buffered saline at 4° C. and filtering the supernatant thereof.

Swamy et al., *Molec. Biochem. Parasit.* 9:1 (1983), report isolated from two acid proteases from adult *D. immitis* extracts.

Grieve et al., *Acta Tropica* 42:63 (1985), report antigens which were solubilized from aqueous-insoluble material of adult female *D. immitis* with a detergent.

SUMMARY OF THE INVENTION

In one aspect, this invention is a vaccine for protecting a mammal from infection by Dirofilaria which comprises an effective, non-toxic amount of a water-soluble fraction and of an acid-soluble fraction of an extract of adult Dirofilaria organisms.

In other aspects, this invention is a process for preparing such vaccine and a method for protecting a mammal from infection by Dirofilaria which comprises internally administering such vaccine to the mammal.

These and other embodiments, which are fully disclosed below, are further aspects of the same invention.

DETAILED DESCRIPTION OF THE INVENTION

Development of a vaccine which constitutes this invention was predicated on the premise that a vaccine should elicit protective antibodies that would be active against the developing parasite prior to the establishment of adult worms and the formation of circulating microfilaria (the pre-patent stage of infection). Since the infectious larvae, as well as the adult worms, have passed through a metamorphosis of development, they contain a plethora of antigenic components, some of which may not elicit detectable and/or protective antibodies and some of which may be repressed as antigenic stimuli unless fractionated out from the multiplicity of antigens of which these intact parasites are composed. The determination as to which antigen(s) would be useful as a vaccine was determined by the fractionation of adult worms in order to discover those antigens which would be representative of antibodies present in the pre-patent stages of the infectious process. Schemes 1 and 2, below, represent procedures utilized to prepare a series of antigenic fractions which, when tested against dog sera from dogs that had been infected at various stages, showed varied activity in detecting circulating antibody.
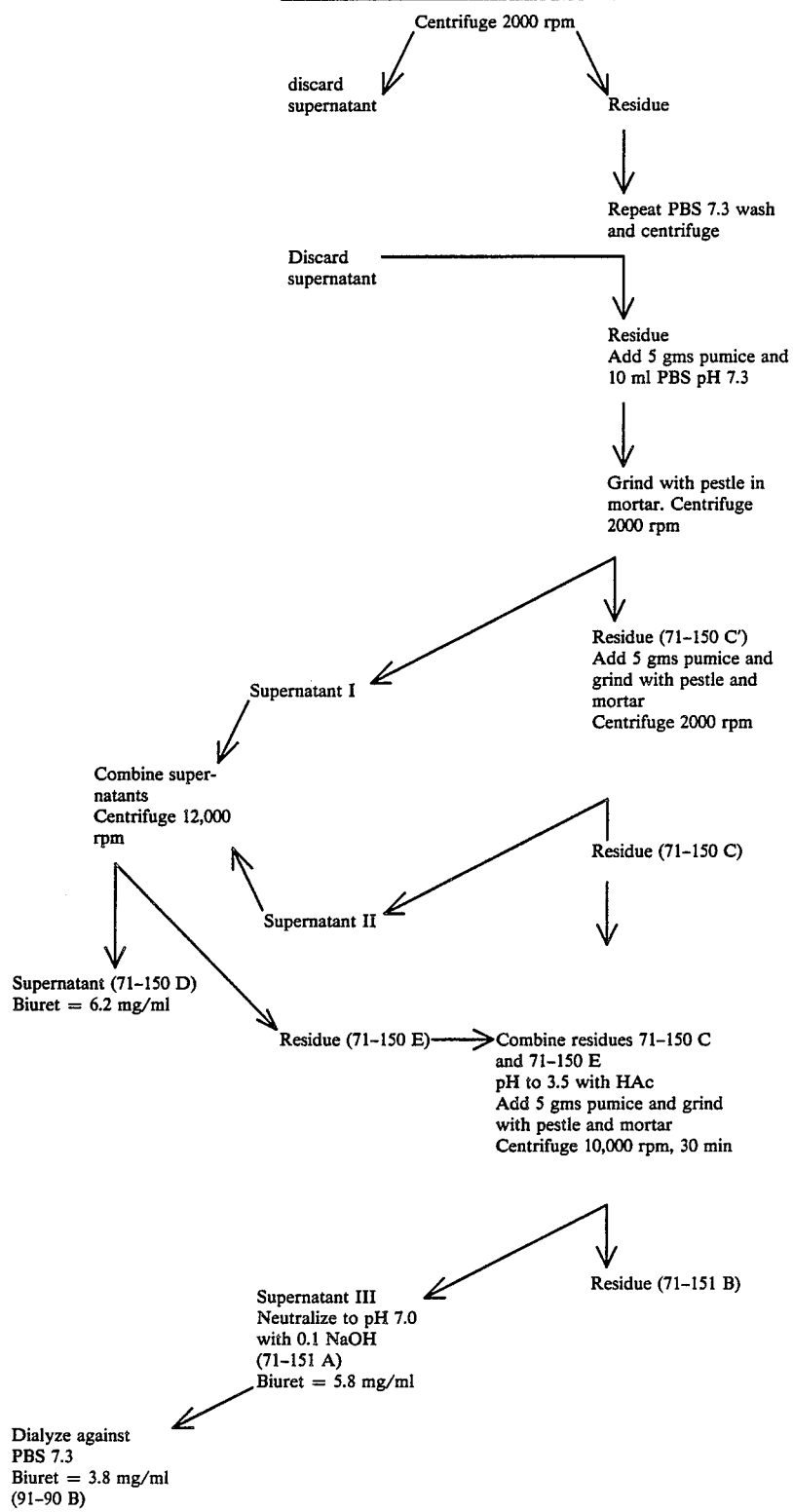

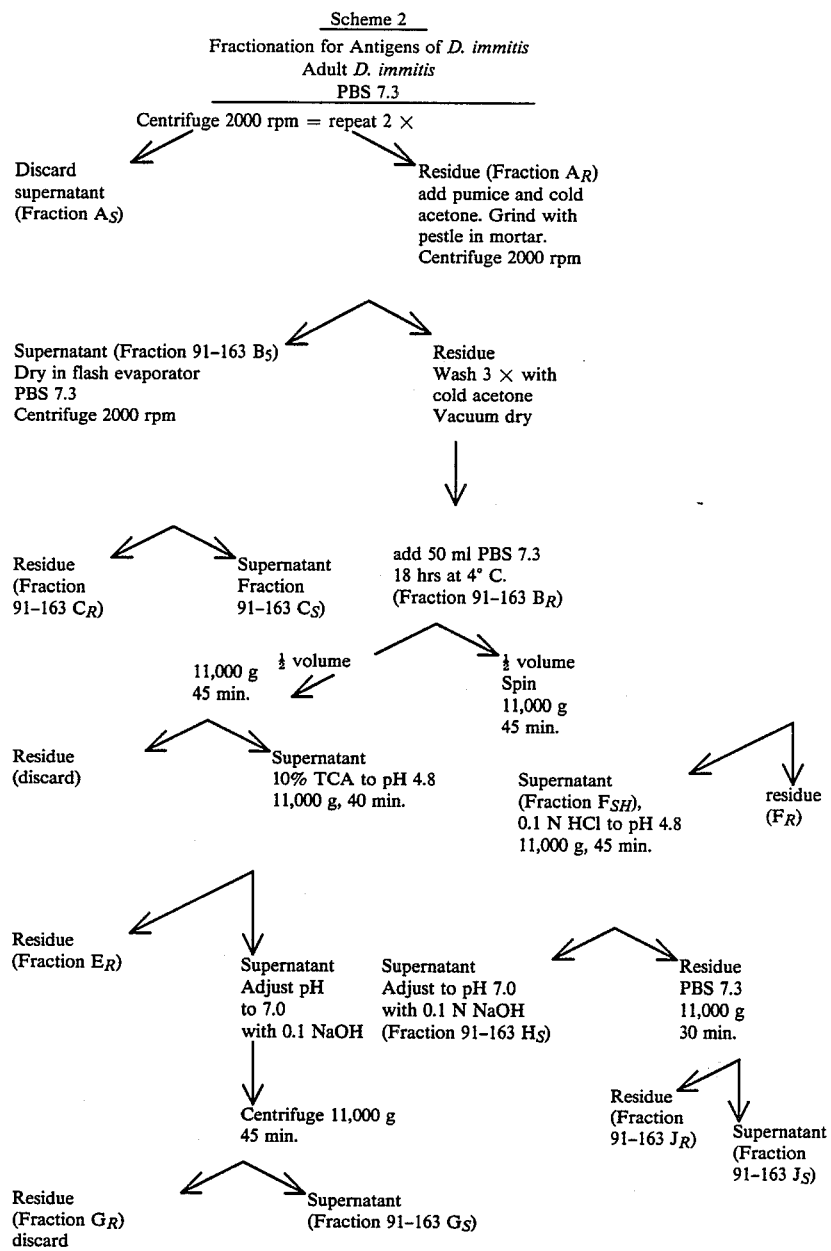

Scheme 2
Fractionation for Antigens of *D. immitis*

It was found that the acid-soluble fractions, e.g., 91-90B in Scheme 1, 91-163$G_S$ in Scheme 2, and 91-163$H_S$ in Scheme 2, were more efficacious in detecting antibody in animals during the early stages of infection whereas the water-soluble fraction, e.g., 71-150D in Scheme 1, was most sensitive in detecting antibody during the latter stages of infection.

To stimulate production of protective antibodies over the prolonged period during the prepatent stage that would interfere with the metamorphosis and development of the parasite prior to the onset of the adult worm in the heart and lungs of an infected animal or man, and/or so that a developing parasite would act as an anemnestic antigenic stimulus for enhanced release of antibodies into circulation which would disrupt continued development of Dirofilaria prior to the adult stage, both the acid-soluble and water-soluble fractions were used to prepare the vaccine of the invention as described in the Examples below.

The vaccine of this invention thus comprises two fractions of adult Dirofilaria extract in a pharmaceutically acceptable carrier. One fraction is water-soluble, meaning that it is soluble in aqueous solvent at about neutral pH, for example, pH 6.5-7.5, as evidenced by the solubility of this fraction in phosphate buffered saline (PBS) at about pH 7. The other is acid-soluble, meaning that it is soluble in aqueous solvent at low pH, for example, pH 3-5, as evidenced by the solubility of this fraction in acids such as hydrochloric acid, trichloracetic acid or acetic acid at about pH 3.5-4.8.

Adult Dirofilaria for use in preparing the vaccine of the invention are available from a variety of sources, including infected animals such as canines. A population of such infective larvae can be maintained by allowing mosquitos, for example, *Aedes aegypti,* to feed on an infected animal. Extracts of Dirofilaria can be prepared by any technique which disrupts the organism and are typically prepared by physical disruption such as grinding. The organisms are preferably washed prior to disruption. Following disruption, one or successive fractions which are soluble in aqueous solution at neutral pH but which are not soluble in aqueous solution at low pH are collected, as are one or successive fractions soluble in aqueous solution at low pH but which are not soluble in aqueous solution at neutral pH. The two fractions are combined in a 10:1 to 1:5 (w/w) water-soluble:acid-soluble ratio, preferably about 4:1 (w/w) water-soluble:acid-soluble. The pH of the vaccine is adjusted such as by addition of base and/or dialysis to prepare a tolerated injectable solution. A preservative such as sodium azide or merthiolate can be added.

The vaccine can be adjuvanted with any adjuvant acceptable for internal administration to the vaccinate. The examples reported below demonstrate that use of a carbohydrate polymer, especially an alginate, as an adjuvant gives an unexpectedly superior immunoprotective response. Alginate is a derivative of alginic acid. Alginic acid is a carbohydrate co-polymer of L-guluronic acid and D-mannuronic acid residues resulting in a polymer structure similar to cellulose. Alginate can be extracted from seaweed. It is also publicly available from other sources, including commercial vendors such as Kelco (Chicago, Ill.). Use of alginate as a vaccine adjuvant is disclosed, for example, by Scherr et al., U.S. Pat. No. 3,075,883; Schechmeister et al., U.S. Pat. No. 3,925,544; and Billiau et al., U.S. Pat. No. 3,839,555. An alginate adjuvant typically comprises 1% to 5% of each vaccine dose.

Other examples of useful carbohydrate polymers are pluronic polyols, L121 & T1501, for example, which are co-polymers of polyoxypropylene and polyoxyethylene. (Hunter et al., *J. Immunol.*:133(6):3167) and polyoxyethylene sorbitan monooleate (Tween 80) and sorbitan monooleate (Span 80) (Woodard et al., *Vaccine* 3: 137).

The vaccine is formulated by dilution with an acceptable excipient, such as normal saline or buffered aqueous solution, or concentrated, such as by dialysis. Vaccines containing up to 5000 μg/dose of the combined fractions from *D. immitis* have been tested and shown to be effective. The preferred dose range is about 0.5 to 200 micrograms/dose, especially about 1–75 micrograms of extract per vaccine dose. The vaccine is administered parenterally, by intramuscular, subcutaneous or intradermal administration. The preferred route of administration in dogs is by subcutaneous injection.

Typically, the vaccine will be administered in two doses, the second dose being about 1 to 6 weeks, preferably about 3 weeks after the first. The dose volume is in the range of 0.5 to 3 ml, preferably about 1 ml. Re-vaccinations can be periodically administered, for example, yearly or bi-annually. Preferably, the initial vaccination is administered prior to infection, that is, to young animals 6 to 8 weeks old or to animals which otherwise have not been exposed.

The antigenic components which comprise the vaccine of this invention can be combined with vaccinal amounts, that is, safe and effective amounts, of other Dirofilaria antigens or with other antigens which can induce an immune response to infection by one or more other pathogenic bacteria, parasite, virus or other invasive microorganism, provided that such additional antigenic components do not significantly adversely affect the immune response to the protective Dirofilaria antigens.

The examples which follow are illustrative, but not limiting, of particular embodiments of this invention. All reagents are commonly available. Alginate was obtained from a commercial source (Kelco, Chicago, Ill.); Quil A is a saponin (see, for example, Dalsgaard, *Acta Vet. Scand.* 18:349–360(1977)) which was purchased from Sepulco (Belletente, Pa.); Montanide 888 is a monooleate which was purchased from Seppic (Paris, France); Polyol 121 was purchased from BASF, Wyandotte, Mich.

EXAMPLES

MATERIALS AND METHODS

A. Source

Mature *Dirofilaria immitis* were collected from the hearts of dogs and stored frozen at −70° C.

B. *Fractionation of D. immitis Vaccine Antigen*

Fractionation of adult heartworm antigen was performed as follows:

Twenty grams of adult heartworm were washed three times in phosphate buffered saline (pH 7.3), placed in a mortar and ground for 15 minutes in the presence of 5 g of pumice rubbing compound (Bordex) and 5 ml of PBS. An additional 5 g of pumice and 5 ml of PBS were added and the contents were ground for an additional 10 minutes.

The contents were centrifuged and the supernatant was removed and stored. The residue was ground again in the presence of 10 g of pumice and 15 ml of PBS.

Following centrifugation, the residue was saved and the supernatant was pooled with the supernatant which had been collected following the first centrifugation.

The pooled supernatants were centrifuged at 12,000 rpm for 30 minutes at 5° C. to pellet the remaining pumice and cell debris. The residue was pooled. The pooled supernatants were centrifuged at 20,000 G to clarify and then were stored at −70° C.

The residues collected above were combined and the pH was adjusted to 3.5 with 40 ml of 20% glacial acetic acid.

Ten additional grams of pumice were added and the contents were ground for 5 minutes and stirred overnight at 4° C.

The supernatant was removed and stored. The top part of the residue in the centrifuge tube (the cell debris) was removed, ground briefly, and the pH was adjusted to 3.5 with acetic acid. The pumice left in the tubes was added to the cell debris, the contents were ground for 5 minutes and then were centrifuged at 20,000 G.

The supernatant was removed and was combined with the supernatant which had been collected following the first centrifugation. The supernatants were centrifuged again at 20,000 G, dialyzed again at 0.85% saline (pH 3.5) and then were stored at −70° C. Protein concentration was determined by the Lowry Procedure.

C. Preparation of Vaccines

All vaccines contained a 4:1 ratio of PBS-soluble to acetic-acid soluble *D. immitis* antigen. The vaccines contained 0.01% merthiolate.

Vaccines were adjuvanted with either alginate, Quil A (Sepulco), Quil A and 50% oil and Montanide 888

(Seppic), or Quil A and 5% oil and polyol L121 (Wyandotte Co.).

D. Vaccination Procedure

Dogs were vaccinated twice either intradermally (ID), subcutaneously (SC), or intramuscularly (IM).

E. Antibody Responses to D. immitis Antigens

Serum of dogs were tested for antibodies to D. immitis by a passive hemagglutination test (PCA). Test and control sera in 25 microliter (ul) volumes were diluted in serial twofold dilutions in U-bottom microtiter plates. With a Pasteur pipette, 35-40 ul of sodium dibasic, potassium monobasic phosphate buffer with 0.5% bovine serum albumin (BSA) was added to each well. One drop from a Pasteur pipette of Dirofilaria immitis-sensitized sheep red blood cells was put in each well and incubated at room temperature overnight (this test can be read after 1 hour). The titer was that dilution of serum which produced visible agglutination.

F. Evaluation of Pathogenicity

Pathogenicity of third stage larval (L3) infection was evaluated in two ways: (1) Ten mosquitos that contained L3 in their salivary glands were macerated and injected SC into each dog in Efficacy Test No. 1; 2) infective L3 were first removed from the salivary glands of mosquitos. Twenty-five larvae were then injected subcutaneously (SC) into each dog in Efficacy Test No. 2.

After 220 days post-infection in Efficacy Test No. 1 and after 199 days post-infection in Efficacy Test No. 2, the dogs were euthanized and their hearts and lungs were examined for adult heartworms.

G. Efficacy Studies

Efficacy was determined by vaccination and challenge studies. The vaccination procedure is described in Section D above, and the evaluation of challenge is described in Section F, above. Serum was collected prior to vaccination and following each vaccination.

1. Efficacy Test No. 1

Five mixed breed littermates, 12 weeks of age (A1-A5), and 6 mixed breed littermates, 4 weeks of age (B1-B5 and B7), were vaccinated. One puppy from each litter (A6 and B6) was selected as non-vaccinated non-infected controls. Two additional dogs, C1 and C2, were vaccinated but not challenged. Two dogs, D1F2 and D2F2 were not immunized but were infected.

All dogs were housed in a barn or in outside runs. They were not screened from mosquitos.

The acetic acid soluble antigen was diluted to a concentration of 1.5 mg/ml of protein. The dogs received 0.1 ml intradermally into 3 separate injection sites and 0.2 ml intramuscularly into 3 separate injection sites on 8-13-80.

On the following day each dog was vaccinated with the PBS-soluble fraction at a concentration of 5 mg/ml. The dogs received 0.1 ml intradermally into 3 separate injection sites followed by 0.2 ml injected intramuscularly into each of 3 injection sites.

Twenty-five days later the vaccinated dogs were immunized a second time and in the same manner.

Serum for serological testing and testing for microfilaria was collected periodically. On the 544th day following vaccination all of the surviving dogs that were vaccinated and two non-vaccinated dogs that had been shown to be free of D. immitis were challenged.

Serum for serological testing and testing for microfilaria was collected periodically following challenge.

2. Efficacy Test No. 2

Seventeen mixed breed dogs and 27 beagles, 3 to 6 months of age, were randomly divided into 10 vaccine groups. All dogs were housed in outside pens. Four groups, consisting of 6 or 3 dogs per group, were inoculated with vaccine antigen adjuvanted with different adjuvants two times, about 3 weeks apart. The adjuvants were: (1) 300 micrograms (μg) Quil A; (2) 300 μg Quil A, 45% oil, 5% Montanide 888; (3) 300 μg Quil A, 5% oil, and 5% polyol 121; and (4) 2.5% alginate. Three dogs in each group were inoculated SC and 3 dogs in 3 of the groups were inoculated IM. Four other vaccine groups were inoculated SC with vaccine consisting of either 40, 4, or 0.4 μg/ml of vaccine antigens adjuvanted with 300 μg Quil A, 45% oil, and 5% Montanide 888 or of 40 μg/ml of antigen with 2.5% alginate. An additional 2 groups of 2 dogs each were inoculated SC with vaccine consisting of either 40 or 4 μg/ml of vaccine antigen adjuvanted with 300 μg Quil A, 45% oil, and 5% Montanide 888.

Serum for serological testing was collected before vaccination, 7, 19 and 21 days post first vaccination and 7, 14, 21, 28, and 56 days post second vaccination. Serum for serological testing was collected from dogs that were challenged at 3, 6, 10, 12, 15, 18, and 21 weeks post challenge.

RESULTS

Efficacy Test No. 1

The passive hemeagglutination (PHA) antibody titers of all dogs except B4 and A6 were low following vaccination (Table 1). Dog A6 was a dog that was neither vaccinated nor challenged. Dog B4 was a vaccinated dog. Its titer remained high after challenge.

All vaccinated dogs except A4 were free of heartworm 173 days post challenge. Microfilaria were detected in the blood of DOG A4 prior to challenge. This dog was evidently naturally infected after being vaccinated. Microfilaria were also detected in the blood of dog A6. This dog was neither vaccinated nor challenged. Mature heartworms were collected from both dogs that were not vaccinated but experimentally infected with D. immitis infective larvae.

TABLE 1

Antibody Response of Dog to D. immitis Antigens Following Vaccination and Challenge
Reciprocal of PHA Titer

| Vaccination Infection Status | Dog No. | Days Post Vaccination | | | | | | Days Post Infection | | | Results of Challenge |
|---|---|---|---|---|---|---|---|---|---|---|---|
| | | 59 | 97 | 234 | 275 | 362 | 543 | 54 | 135 | 173 | Presence of Heartworm |
| Vaccinated and Challenged | A1[1] A2[2] | 71 | <71 | 71 | 192 | 71 | 192 | 192 | 71 | 71 | — |

TABLE 1-continued

Antibody Response of Dog to *D. immitis* Antigens Following Vaccination and Challenge
Reciprocal of PHA Titer

| Vaccination Infection Status | Dog No. | Days Post Vaccination | | | | | | Days Post Infection | | | Results of Challenge Presence of Heartworm |
|---|---|---|---|---|---|---|---|---|---|---|---|
| | | 59 | 97 | 234 | 275 | 362 | 543 | 54 | 135 | 173 | |
| | A3[2] | | | | | | | | | | |
| | A4 | 71 | 71 | 0 | 71 | 192 | 192[3] | | | | + |
| | A5 | 71 | ND | 516 | 192 | 192 | 192 | 192 | 192 | ND | — |
| | B1 | 0 | 71 | 0 | 71 | 71 | 71 | ND | ND | ND | — |
| | B2 | 71 | 71 | 192 | 192 | 192 | 71 | 71 | 71 | 71 | — |
| | B3[3] | | | | | | | | | | |
| | B4 | ND | 71 | 192 | 516 | 1341 | 516 | 1341 | 516 | 516 | — |
| | B5 | 0 | 71 | 192 | 516 | 192 | 192 | 192 | 192 | 192 | — |
| | B7 | 0 | 71 | 01192 | | 71 | 71 | 71 | 71 | 71 | — |
| Not Vaccinated | A6 | 0 | 0 | 71 | 192 | 516 | 1341[3] | | | | + |
| Not Challenged | B6[2] | 0 | 0 | 71 | | | | | | | |
| Vaccinated | C1 | 0 | 71 | 192 | 192 | 71 | 71 | 71 | 71 | 71 | — |
| Not Infected | C2 | 0 | 0 | 71 | 192 | ND | 192 | 71 | 71 | 71 | — |
| Not Vaccinated | D1F2 | | | | | | | 71 | 516 | 516 | + |
| Infected | D2F2 | | | | | | | 71 | 192 | 192 | + |

[1] Vaccinated dogs on Days 0, 1, 25, 27. Infected dogs on Day 594
[2] A2 found dead on Day 62, no autopsy.
A3 found dead on Day 103, no autopsy.
B3 found dead on Day 93, no autopsy.
B6 found dead on day 254, autopsy, no adult heartworms, no micorfilaria.
[3] Micofilaria detected in blood before dog was infected.

Efficacy Test No. 2

All dogs inoculated either SC or intramuscularly (IM) with 100 or 200 µg of the vaccine antigen adjuvanted with either Quil A, Quil A 45% oil, and Montanide 888, or 5% oil and polyol L121 developed an antibody response to heartworm antigen (Table 2). Dogs inoculated SC with 40, 4 or 0.4 µg heartworm antigen per dose and adjuvanted with quil A, 45% oil, and Montanide 888 also showed increased anti-heartworm antibody titers following vaccination, particularly the second vaccination (Tables 3 and 4).

TABLE 2

Effect of Different Adjuvants and Route of Vaccination on the Antibody Response of Dogs to Heartworm Antigen

| Adjuvant | Antigen Concentration (µg/ml) | Route | Dog No. | Geometric Mean Hemaglutination Titer | | | | | | | | |
|---|---|---|---|---|---|---|---|---|---|---|---|---|
| | | | | Days Post First Vaccination | | | | Days Post Second Vaccination | | | | |
| | | | | 0 | 7 | 14 | 21 | 7 | 14 | 21 | 28 | 56 |
| Quil A[1] | 100 | SC | DB44 | 32 | 64 | 256 | 128 | 1024 | 256 | 256 | 32 | 112 |
| | | | DA26 | 24 | 64 | 128 | 128 | 2048 | 137 | 256 | 128 | 160 |
| | | | DB3 | 12 | 46 | 256 | 128 | 168 | 137 | 256 | 128 | 109 |
| GM Titer | | | | 21 | 73 | 203 | 128 | 1172 | 169 | 256 | 81 | 127 |
| Quil A[1] | 100 | IM | OIA3 | 64 | 64 | 512 | 256 | 3072 | >2560 | 168 | 512 | 672 |
| | | | HUA3 | 64 | 48 | 384 | 192 | 1536 | 512 | 384 | 128 | 192 |
| | | | PFA3 | 64 | 32 | 256 | 256 | 2098 | 512 | 96 | 512 | 160 |
| GM Titer | | | | 64 | 46 | 369 | 233 | 2130 | >876 | 305 | 323 | 274 |
| Quil A[1] M888[2], Oil[3] | 100 | SC | LEA3 | 48 | 384 | 1024 | 1024 | 1536 | 768 | >1536 | 256 | 373 |
| | | | OVA3 | 64 | 64 | 354 | 256 | 8192 | 512 | 512 | 768 | 405 |
| | | | IVA3 | 32 | 96 | 10224 | 384 | 1024 | 768 | 192 | 192 | 181 |
| GM Titer | | | | 46 | 133 | 738 | 465 | 2344 | 671 | >533 | 335 | 301 |
| Quil A[1] M888[2], Oil[3] | 100 | IM | WDF3 | 32 | 48 | 384 | 1536 | 768 | 768 | 256 | 256 | 384 |
| | | | WJF3 | 16 | 64 | 512 | 192 | 2048 | 512 | 256 | 256 | 224 |
| | | | XKF3 | 128 | >384 | 512 | 1024 | 4096 | 640 | >1536 | 768 | >795 |
| GM Titer | | | | 40 | >106 | 465 | 671 | 1861 | 631 | >465 | 369 | >409 |
| Quil A[1] Polyol[L121, 4] Oil[5] | 100 | SC | XXF3 | 32 | 64 | 1536 | 1024 | >12288 | 768 | 512 | 768 | >850 |
| | | | QYD3 | 16 | 96 | 512 | 128 | 2048 | 1024 | 384 | 128 | 107 |
| | | | WYF3 | 128 | 32 | 512 | 128 | 1536 | 192 | 384 | 384 | 256 |
| GM Titer | | | | 40 | 58 | 738 | 256 | >3381 | 533 | 423 | 335 | 284 |
| Quil A[1] Polyol[L121] Oil[5] | 100 | IM | DB2 | 128 | 16 | 128 | 96 | 512 | 256 | 192 | 128 | 56 |
| | | | DB27 | 32 | 12 | 192 | 128 | 1536 | 256 | 64 | 96 | 91 |
| | | | DB22 | 64 | 32 | 384 | 384 | 2048 | 768 | 512 | 96 | 235 |
| GM Titer | | | | 64 | 18 | 211 | 168 | 1172 | 369 | 185 | 106 | 106 |
| Alginate | 200 | SC | 26 | 32 | 48 | 24 | 48 | 192 | 96 | 128 | 128 | 144 |
| | | | 1 | 16 | 16 | 48 | 64 | 48 | 64 | 1024 | 32 | 32 |
| | | | DA48 | 48 | ND | 32 | 64 | 96 | 48 | 96 | 64 | 96 |
| GM Titer | | | | 29 | 28 | 33 | 58 | 96 | 27 | 233 | 64 | 76 |

[1] 300 µg Quil A per dose
[2] 5% Montanide 888
[3] 45% Drakeol 6VR oil
[4] 5% Polyol L121
[5] 5% Drakeol 6VR oil

TABLE 3

Effect of Adjuvant and Antigen Concentration on the HA Titer of Dogs to *D. immitis* Antigen

| Adjuvant | Antigen Concentration μg/ml | Dog No. | Geometric Mean Hemaglutination Titer | | | | | | | | |
|---|---|---|---|---|---|---|---|---|---|---|---|
| | | | Days Post First Vaccination | | | | Days Post Second Vaccination | | | | |
| | | | 0 | 7 | 14 | 21 | 7 | 14 | 21 | 28 | 56 |
| Alginate | 40 | 94 | 12 | 64 | 32 | 64 | 32 | 64 | 96 | 24 | 48 |
| | | 83 | 8 | 32 | 16 | 32 | 96 | 32 | 64 | 32 | 96 |
| | | 80 | 12 | 64 | 48 | 64 | 48 | 64 | 128 | 64 | 48 |
| | Geometric Mean | | 10 | 51 | 29 | 51 | 53 | 52 | 92 | 37 | 60 |
| | | 55 | 32 | 32 | 64 | 128 | 128 | 192 | 256 | 192 | 64 |
| | 40 | 100 | ND | 96 | 96 | 128 | 256 | 256 | 1024 | 512 | 84 |
| | | 81 | 16 | 64 | 24 | 64 | 256 | 384 | 96 | 256 | 192 |
| | Geometric Mean | | 23 | 58 | 53 | 101 | 203 | 266 | 293 | 293 | 168 |
| Quil A/ Drakeol Oil/ Montanide 888 | 4 | 53 | 16 | 32 | 32 | 192 | 768 | 512 | 1024 | 768 | 1536 |
| | | 73 | ND | 96 | 64 | 128 | 128 | 96 | 128 | 32 | 192 |
| | | 90 | 128 | 64 | 64 | 128 | 32 | >768 | 768 | 768 | 384 |
| | Geometric Mean | | 45 | 58 | 51 | 128 | 147 | >335 | 465 | 266 | 484 |
| | | 121 | ND | 128 | 24 | 32 | 64 | 64 | 128 | 32 | 48 |
| | 0.4 | DA49 | 128 | 48 | 64 | 96 | 128 | 32 | 256 | 48 | 192 |
| | | DA47 | 48 | 64 | 24 | 64 | 48 | 32 | 128 | 48 | 64 |
| | Geometric Mean | | 78 | 73 | 33 | 58 | 23 | 40 | 161 | 42 | 84 |

TABLE 4

Response of Dogs to 40 μg of Heartworm Vaccine Adjuvanted with Quil A (300 μg) and 5% Drakeol Oil

| Route of Vaccination | Dog No. | Days Post First Vaccination | | | | Days Post Second Vaccination | | | | |
|---|---|---|---|---|---|---|---|---|---|---|
| | | 0 | 7 | 14 | 21 | 7 | 14 | 21 | 28 | 56 |
| Sc | 88 | 24 | 48 | 512 | 384 | 768 | 1024 | 512 | 512 | 192 |
| | 124 | 16 | 64 | 384 | 768 | 2048 | 768 | 512 | 512 | 192 |
| Geometric Mean Titer | | 20 | 55 | 443 | 543 | 1254 | 887 | 627 | 512 | 192 |
| IM | 108 | 16 | 128 | 192 | 96 | 128 | 256 | 192 | 256 | 128 |
| | 102 | 48 | 256 | >1536 | >1536 | 1024 | 1536 | 512 | 512 | 192 |
| Geometric Mean Titer | | 23 | 181 | >543 | >384 | 326 | 627 | 314 | 362 | 257 |

Efficacy Test No. 2 (Cont.)

Increases in PHA anti-heartworm antigen antibody titers following challenge infection and results of challenge are shown in Tables 5 and 6. Most vaccinated dogs responded to challenge with an increase in PHA titer. Dogs inoculated with vaccine containing Quil A, 45% oil and Montanide 888 developed the highest antibody titers post challenge as they did post vaccination. Dogs inoculated with vaccine adjuvanted with alginate showed the smallest increase in antibody titer following challenge.

The 3 dogs that were inoculated with vaccine antigen adjuvanted with alginate, however, were all free of adult heartworm at the time of necropsy. One of three dogs inoculated IM and 1 of 3 dogs inoculated SC with vaccine antigen adjuvanted with Quil A, 5% oil and polyol 121 were also protected from infection. Only 1 other vaccinated dog was free of heartworm following challenge. This dog was inoculated SC with 4 μg of vaccine antigen adjuvanted with Quil A, 45% oil, and 5% Montanide 888.

None of the non-vaccinated challenge control dogs were free of adult heartworms.

TABLE 5

Effect of Different Adjuvants and Route of Vaccination on the Response of Vaccinated Dogs to Challenge

| Adjuvant | Route | Dog No. | Reciprocal of HA Titer Weeks Post Challenge | | | | | | | | Results of Challenge (Number of Heartworms) |
|---|---|---|---|---|---|---|---|---|---|---|---|
| | | | 0 | 3 | 6 | 10 | 12 | 15 | 18 | 21 | |
| Quil A[1] | SC | DB44 | 128 | 64 | 24 | 64 | 48 | 96 | 64 | 64 | 13 |
| | | DA26 | 768 | 96 | 256 | 128 | 128 | 64 | 64 | ND | 3 |
| | | DB3 | 192 | 128 | 64 | 128 | 96 | 48 | 32 | 96 | 1 |
| GM Titer | | | 266 | 92 | 73 | 102 | 84 | 67 | 51 | 78 | |
| Quil A[1] | IM | OIA3 | 384 | 512 | 384 | 128 | 128 | 192 | 768 | 4096 | 13 |
| | | HUA3 | 384 | 256 | 128 | 128 | 192 | 256 | 384 | 512 | 6 |
| | | PFA3 | 32 | 768 | 512 | 256 | 96 | 192 | >2048 | ND | 7 |
| GM Titer | | | 168 | 465 | 293 | 161 | 133 | 211 | >845 | 1448 | |
| Quil A[1] M888 Oil | SC | LEA3 | 64 | 192 | 512 | 512 | 192 | 192 | 192 | 512 | 4 |
| | | CVA3 | 256 | 1024 | 768 | 512 | 768 | 192 | >2048 | 1024 | 17 |
| | | IVA3 | 192 | 96 | 256 | 384 | 384 | 128 | 1024 | 384 | 11 |
| GM Titer | | | 147 | 266 | 465 | 465 | 384 | 168 | >738 | 586 | |
| Quil A[1] M888 Oil | IM | WDF3 | 96 | 768 | 512 | 512 | 512 | 256 | 384 | 4096 | 11 |
| | | WJF3 | 40 | 192 | 192 | 256 | 64 | 96 | 128 | 384 | ND(+)[4] |
| | | XKF3 | 48 | 192 | 512 | 512 | 64 | 128 | 128 | 768 | ND(+)[4] |
| GM Titer | | | 57 | 305 | 369 | 406 | 128 | 147 | 185 | 1065 | |
| Quil A[1] | SC | XXF3 | 64 | 512 | 1024 | 768 | 192 | 192 | 512 | 512 | 4 |

TABLE 5-continued

Effect of Different Adjuvants and Route of Vaccination on the Response of Vaccinated Dogs to Challenge

| Adjuvant | Route | Dog No. | 0 | 3 | 6 | 10 | 12 | 15 | 18 | 21 | Results of Challenge (Number of Heartworms) |
|---|---|---|---|---|---|---|---|---|---|---|---|
| Polyol Oil | | QYD3 | 48 | 256 | 384 | 192 | 192 | 96 | 192 | 128 | 0 |
| | | WYF3 | 48 | 128 | 192 | 96 | 96 | 128 | 384 | 512 | 10 |
| GM Titer | | | 53 | 256 | 423 | 242 | 152 | 133 | 335 | 323 | |
| Quil A[1] | IM | DB2 | 24 | 96 | 48 | 64 | 192 | 96 | 192 | 512 | 0 |
| Polyol Oil | | DB27 | 96 | 192 | 128 | 64 | 64 | 24 | 256 | 192 | 6 |
| | | DB22 | 32 | 512 | 512 | 128 | 256 | 128 | 256 | ND | 2 |
| GM Titer | | | 42 | 211 | 147 | 81 | 147 | 67 | 233 | 314 | |
| Alginate[2] | SC | 26 | 69[3] | 48 | 96 | 32 | 128 | 32 | 96 | 192 | 0 |
| | | 1 | 16 | 24 | 48 | 48 | 32 | 32 | 192 | 384 | 0 |
| | | DA48 | 32 | 32 | 256 | 96 | 128 | 384 | 512 | ND | 0 |
| GM Titer | | | 32 | 33 | 106 | 53 | 81 | 73 | 211 | 272 | |
| Non-Vaccinates | | DA88[3] | 192 | 512 | 384 | 96 | 48 | 64 | 128 | 192 | 22 |
| | | 10 | 32 | 32 | 64 | 48 | 48 | 24 | 32 | 67[4] | 6 |
| | | CT24 | 48 | 96 | 96 | 96 | 128 | 96 | 128 | 384 | 4 |
| | | CT25 | 32 | 64 | 128 | 32 | 64 | 32 | 128 | 192 | 4 |
| | | 132 | 32 | 32 | 32 | 24 | 48 | 48 | 128 | 64 | 14 |
| | | 138 | 32 | 24 | 32 | 32 | 48 | 32 | 384 | 512 | ND(+)[4] |
| | | 147 | 64 | 32 | 96 | 64 | 128 | 128 | >2048 | 384 | ND(+)[4] |
| | | 144 | 16 | 50 | 32 | 128 | 1024 | 192 | 1024 | 516[4] | 8 |
| GM Titer | | | 42 | 50 | 75 | 55 | 93 | 60 | >226 | 222 | |

[1]Challenged 17 weeks post 2nd vaccination. Dogs were vaccinated with 100 μg/ml dose of heartworm antigen.
[2]Challenged 11 weeks post 2nd vaccination. Dogs were vaccinated with 200 μg/ml dose of heartworm antigen.
[3]This dog was probably exposed to D. immitis prior to challenge.
[4]Dogs not necropsied but have Microfilaria in their blood.

TABLE 6

Effect of Concentration of Heartworm Antigen on the Response of Dogs to D. immitis

| Protein Concentration of Antigen[2] (μg/1 ml dose) | Weeks Post 2nd Vacc. | Dog No. | 0 | 3 | 6 | 10 | 12 | 15 | 18 | 21 | Route of Challenge (No. of Heartworms) |
|---|---|---|---|---|---|---|---|---|---|---|---|
| 100 | 17 | LEA3 | 64 | 192 | 512 | 512 | 192 | 192 | 192 | 512 | 4 |
| | | OVA3 | 256 | 1024 | 768 | 512 | 768 | 192 | >2048 | 1024 | 17 |
| | | IVA3 | 192 | 96 | 256 | 384 | 384 | 128 | 1024 | 384 | 11 |
| GM Titer | | | 147 | 266 | 465 | 465 | 384 | 168 | >738 | 586 | |
| 40 | 11 | 55 | 64 | 128 | 96 | 256 | 64 | 192 | 192 | 3072 | 13 |
| | | 100 | 192 | 256 | 512 | 192 | 256 | 512 | 1024 | 768 | 7 |
| | | 81 | 256 | >3072 | 1024 | 512 | 128 | 48 | 192 | 768 | 24 |
| GM Titer | | | 147 | >465 | 369 | 293 | 128 | 168 | 335 | 1219 | |
| 0.4 | 11 | 121 | 16 | 16 | 64 | 32 | 192 | 384 | 384 | 256 | 8 |
| | | DA49 | 16 | 128 | 128 | 64 | 96 | 128 | 256 | 192 | 10 |
| | | DA47 | 24 | 32 | 128 | 128 | 64 | 32 | 96 | 192 | 14 |
| GM Titer | | | 18 | 32 | 102 | 128 | 106 | 116 | 211 | 211 | |
| | | DA88[3] | 192 | 512 | 384 | 96 | 48 | 64 | 128 | 192 | 22 |
| | | 10 | 32 | 32 | 64 | 48 | 48 | 24 | 32 | 64 | 6 |
| | | CT24 | 48 | 96 | 96 | 96 | 128 | 96 | 128 | 384 | 4 |
| | | CT25 | 32 | 64 | 128 | 32 | 64 | 32 | 128 | 192 | 4 |
| | | 132 | 32 | 32 | 32 | 24 | 48 | 48 | 128 | 64 | 14 |
| | | 138 | 32 | 24 | 32 | 32 | 48 | 32 | 384 | 512 | ND(+)[4] |
| | | 137 | 64 | 32 | 96 | 64 | 128 | 128 | >2048 | 384 | ND(+)[4] |
| | | 144 | 16 | 16 | 32 | 128 | 1024 | 192 | 1024 | 512 | 8 |
| GM Titer | | | 42 | 50 | 75 | 55 | 93 | 60 | >226 | 222 | |

[1]Alginate group in Table 3 not challenged.
[2]Heartworm antigen is adjuvanted with Quil A (300 μg/ml) in a water-in-oil emulsion containing Montanide 888. The vaccines were administered SC.
[3]This dog was probably exposed to D. immitis before challenge.
[4]Dogs not necropsied but have microfilaria in their blood.

The preceding examples demonstrate discovery of a vaccine that will aid in the prevention of parasitic disease caused by Dirofilaria and, in particular, of heartworm in dogs. The efficacy of the vaccine was measured by the protection of dogs against a challenge of 60 infective third stage larvae (L3) of D. immitis.

The vaccine antigen, adjuvanted in different ways, stimulated the production of serum antibodies that were detected by the PHA antibody test. However, some vaccines did not stimulate as great an antibody response as others. Vaccine antigen adjuvanted with alginate stimulated very low levels of anti-heartworm antibody compared to vaccine antigen adjuvanted with other adjuvants, particularly, Quil A combined with 45% oil and 5% Montanide 888 (Table 2).

Although high levels of anti-heartworm antibody was found in the serum of dogs inoculated with vaccine antigen adjuvanted with Quil A, oil and Montanide 888, these antibodies were not associated with enhanced protection against challenge. Dogs that were best protected against challenge were dogs that had comparatively low levels of antibody following both vaccination and challenge. The vaccine antigen was most effective as an aid in the prevention of heartworm when it was adjuvanted with one of the two carbohydrate polymers, especially alginate. Six of 7 dogs (86%) in Efficacy Test No. 1, and 3 of 3 dogs (100%) in Efficacy Test No. 2 that were inoculated with vaccine antigen adjuvanted with alginate were protected against challenge. Two of 6 dogs that were inoculated with heartworm antigen and an adjuvant containing polyol L121 were also protected against challenge. One hundred percent (10/10) of infected but non-vaccinated dogs were found to have adult heartworm.

Results of Efficacy Test No. 2 suggested that low concentrations of antigen (100 µg/dose) protect against challenge. One heartworm free vaccinate was inoculated with only 4 µg antigen. This antigen was adjuvanted with Quil A, oil, and Montanide 888.

The above description and examples illustrate particular constructions including the preferred embodiments of the solution. However, the invention is not limited to the precise constructions described herein but, rather, encompasses all modifications and improvements thereof encompassed within the scope of the claims which follow.

I claim:

1. A vaccine for protecting a mammal against infection by Dirofilaria which comprises an effective, non-toxic amount of water-soluble fraction of an extract of adult Dirofilaria organisms and of an acid-soluble fraction of an extract of adult Dirofilaria organisms.

2. The vaccine of claim 1 for protecting a canine animal against infection by D. immitis wherein the extract is of adult D. immitis organisms.

3. The vaccine of claim 2 wherein the water-soluble fraction is soluble at pH 6.5 to 7.5 and the acid-soluble fraction is soluble at pH 3 to 5 and the ratio by weight of the water-soluble fraction to acid-soluble fraction is 10:1 to 1:5.

4. The vaccine of claim 3 in which the ratio by weight of water-soluble fraction to acid-soluble fraction is about 4:1.

5. The vaccine of claim 3 or 4 which is adjuvanted.

6. The vaccine of claim 5 wherein the adjuvant is a carbohydrate polymer.

7. The vaccine of claim 6 in which the adjuvant is 1% to 5% alginate.

8. The vaccine of claim 4 in a 0.5 to 3 ml dosage unit in which the combined amount of water-soluble and acid-soluble fractions is 0.5 to 200 µg, in saline buffered to pH 6.5 to 7.5, the vaccine is adjuvanted with 2.5% alginate and the vaccine contains about 0.01% merthiolate.

9. A process for preparing a vaccine for protecting a mammal against infection by Dirofilaria which comprises (i) disrupting Dirofilaria adult heartworms to prepare an extract thereof; (ii) separately collecting a water soluble fraction thereof and an acid-soluble fraction thereof and (iii) combining the two fractions in a pharmaceutically acceptable carrier.

10. The process of claim 9 in which the Dirofilaria adult heartworms are Dirofilaria immitis.

11. The process of claim 9 in which the water-soluble fraction is soluble at pH 6.5 to 7.5 and the acid-soluble fraction is soluble at pH 3 to 5 and the ratio by weight of the water-soluble fraction to acid-soluble fraction is 10:1 to 1:5.

12. The process of claim 10 in which, in step (iii), the two fractions are combined in a ratio of about 4:1 (w/w) water-soluble:acid soluble.

13. The process of claim 10 or 11 which further comprises combining the water-soluble and acid-soluble fractions with an adjuvant.

14. The process of claim 13 in which the adjuvant is a carbohydrate polymer.

15. The process of claim 13 in which the adjuvant is 1% to 5% alginate.

16. The process of claim 12 in which the combined amount of water-soluble and acid-soluble fractions is 0.5 to 200 µg per dose volume, the dose volume being 0.5 to 3 ml; the vaccine is buffered to pH 6.5 in saline, the vaccine is adjuvanted with 2.5% alginate; and, about 0.01% merthiolate is added to the vaccine.

17. A method for eliciting an immune response in a mammal to Dirofilaria which comprises internally administering to the mammal an effective, non-toxic amount of a water-soluble fraction of an extract of adult Dirofilaria organisms and of an acid-soluble fraction of an extract of adult Dirofilaria organisms.

18. The method of claim 17 for protecting a canine animal against infection by D. immitis wherein the extract is of adult D. immitis organisms.

19. The method of claim 17 wherein the water soluble fraction is soluble at pH 6.5 to 7.5 and the acid-soluble fraction is soluble at pH 3–5 and the ratio by weight of the water-soluble fraction to acid-soluble fraction is 10:1 to 1:5.

20. The method of claim 18 in which the ratio by weight of water-soluble fraction to acid-soluble fraction is about 4:1.

21. The method of claim 18 or 19 in which the water-soluble and acid-soluble fractions are administered with an adjuvant.

22. The method of claim 21 in which the adjuvant is a carbohydrate polymer.

23. The method of claim 21 in which the adjuvant is 1% to 5% alginate.

24. The method of claim 20 in which the combined amount of water-soluble and acid-soluble fractions is 0.5 to 200 µg per dose volume, the dose volume being 0.5 to 3 ml; the vaccine is buffered to pH 6.5 in saline, the vaccine is adjuvanted with 2.5% alginate; and, about 0.01% merthiolate is added to the vaccine.

* * * * *

UNITED STATES PATENT AND TRADEMARK OFFICE
CERTIFICATE OF CORRECTION

PATENT NO. : 4,761,281
DATED : August 2, 1988
INVENTOR(S) : George H. Scherr

It is certified that error appears in the above-identified patent and that said Letters Patent are hereby corrected as shown below:

Column 18, line 20, "oombined" should read --combined--.

Signed and Sealed this

Tenth Day of January, 1989

Attest:

DONALD J. QUIGG

*Attesting Officer*    *Commissioner of Patents and Trademarks*